United States Patent
Nakamura et al.

[11] Patent Number: 6,106,691
[45] Date of Patent: Aug. 22, 2000

[54] MEDICAL INSTRUMENT STERILIZING AND WASHING METHOD AND APPARATUS

[75] Inventors: Shinichi Nakamura, Osaka; Kunihiko Hukuzuka, Habikino; Hiromi Fujii, Osaka, all of Japan

[73] Assignee: T.R.P Co., Ltd., Osaka-fu, Japan

[21] Appl. No.: 09/041,533

[22] Filed: Mar. 12, 1998

[30] Foreign Application Priority Data

Feb. 12, 1998 [JP] Japan .................................. 10-046239

[51] Int. Cl.⁷ .............................. A61L 2/03; C02F 1/461; C25B 1/24
[52] U.S. Cl. ......................... 205/701; 205/499; 205/742; 204/228.6; 204/229.2; 204/229.4; 134/26; 134/28; 422/28; 422/292; 422/294
[58] Field of Search ................ 134/26; 204/242, 204/228.6, 229.2, 229.4; 210/62; 205/701, 742, 499; 422/28, 294, 292

[56] References Cited

U.S. PATENT DOCUMENTS

| | | | |
|---|---|---|---|
| 2,882,210 | 3/1959 | Jenks | 204/151 |
| 5,425,815 | 6/1995 | Parker et al. | 134/26 |
| 5,429,723 | 7/1995 | Atkinson | 204/103 |
| 5,449,442 | 9/1995 | Yamada et al. | 204/130 |

FOREIGN PATENT DOCUMENTS

| | | |
|---|---|---|
| 0243846 | 11/1987 | European Pat. Off. . |
| 3502068 | 5/1991 | Japan . |
| 7275811 | 10/1995 | Japan . |
| 966064 | 3/1997 | Japan . |
| 9108307 | 4/1997 | Japan . |

Primary Examiner—Kathryn Gorgos
Assistant Examiner—Thao Tran
Attorney, Agent, or Firm—Hayes, Soloway, Hennessey, Grossman & Hage, P.C.

[57] ABSTRACT

In a medical instrument sterilizing and washing method and apparatus for sterilizing and washing a medical instrument in a short time without corroding the metal forming the medical instrument to be washed. The sterilizing and washing method comprises the steps of preparing an electrolytic aqueous solution by adding and dissolving a halide composed of a bromide compound as a simple substance or a bromide compound and other halogenated compound to and in tap water; directly subjecting the electrolytic aqueous solution to electrolysis through electrode plates composed of an anode and a cathode and generating electrolytically-generated water containing hypohalogenous acid; and sterilizing and washing the medical instrument with the electrolytically-generated water while maintaining the hydrogen ion concentration (pH) in the electrolytic water to at least 6 at all times.

12 Claims, 8 Drawing Sheets

MEDICAL INSTRUMENT STERILIZING AND WASHING METHOD AND APPARATUS

BACKGROUND OF THE INVENTION

1. Field of the Invention

The present invention relates to a medical instrument sterilizing and washing method and apparatus capable of easily sterilizing and washing medical instruments in a short time without corroding the medical instruments and in particular, even medical instruments such as endoscopes and the like which are composed of the combination of metal, resin and the like, formed to a complex shape, directly used in a living body and greatly contaminated with dirty materials and germs.

2. Description of the Related Art

Conventionally, medical instruments and in particular, endoscopes and the like which are directly used in a living body are contaminated with blood and body fluid and further very liable to be contaminated with various types of germs. Accordingly, they must be sterilized and washed each time they are used.

A most effective prior art method of sterilizing and washing the medical instruments is heat sterilization and has been widely used up to now. Recently, however, there has been an abrupt increase in the number of medical instruments such as the endoscopes and the like which are composed of resin, rubber and the like in addition to metal. Since these medical instruments employing resin, rubber and the like cannot be subjected to heat sterilization, they are sterilized and washed with a glutaaldehyde antiseptic solution.

However, since glutaaldehyde antiseptic solution is a powerful medicine, sterilizing and washing using it presents certain problems such as; the glutaaldehyde antiseptic solution affects the skin affection and lungs of a worker who performs washing with it when he comes into contact with and inhales the liquid medicine; since post washing is necessary to wash the liquid medicine away after completion of the sterilizing and washing, a long time is necessary for a sterilizing processing; a sufficient sterilizing effect cannot be achieved against germs, viruses and the like which are resistant to gluta aldehyde antiseptic solution; and hospital contamination may be caused in a worst case.

There has been proposed using as an antiseption solution electrolytically-generated super-acidic water with strong acidity which is generated by electrolyzing water in which sodium chloride is dissolved. See Japanese Unexamined Patent Publication No. 7-275811, Japanese Unexamined Patent Publication No. 9-66064 and Japanese Unexamined Patent Publication No. 9-108307.

Since of using electrolytically-generated strongly acidic water has no adverse affect to the operator and does not require post washing, time and manpower necessary for sterilization processing can be reduced. A problem, however, with using electrolytically generated strongly acid water as the sterilizing solution is that the metal constituting a medical instrument to be washed, for example, stainless steel such as SUS 304 and the like which is often used to form medical instruments is corroded by electrolytically-generated strongly acidic water. When the electrolytically-generated strongly acidic water is used under conditions that the pH thereof is increased by dilution or the like or the concentration of residual chlorine is lowered by lowering the concentration of additive sodium chloride to lower the corrosion caused by the strongly acidic water, there arises a problem that a sufficient sterilizing capability cannot be obtained and/or a longer processing time is required.

An object of the present invention is to provide a medical instrument sterilizing and washing method and apparatus capable of sterilizing and washing medical instruments with a high sterilizing capability in a short time without corroding the metal of the medical instrument being washed.

SUMMARY OF THE INVENTION

To solve the above problems, a medical instrument sterilizing and washing method of the present invention comprises the steps of preparing an electrolytic aqueous solution by adding and dissolving a halide composed of a bromine compound as a simple substance or a bromine compound and other halogenated compound to and in tap water; directly subjecting the electrolytic aqueous solution to electrolysis through electrode plates composed of an anode and a cathode and generating electrolytically-generated water containing hypohalogeneous acid; and sterilizing and washing a medical instrument by causing the electrolytically-generated water to come into contact with the materials deposited to the medical instrument while maintaining the pH in the electrolytic water at least 6 at all times.

According to the above feature, since the hypobromous acid as hypohalogenous acid generated by the electrolysis exists in the electrolytically-generated water at a high ratio even if the pH is at least 6, the electrolytically-generated water can wash and sterilize organic stains, germs, viruses and the like deposited on the used medical instruments due to the strong oxidizing action of the hypohalogenous acid and the electrolytically-generated water without corroding the metal and the like of the medical instrument because the pH thereof is at least 6.

In the medical instrument sterilizing and washing method according to the present invention, it is preferable that the halogen ion supplied by the halide electrolyte are bromide ion and chloride ion and they are used in a mole ratio within the range of 6:4 to 1:9.

With this arrangement, since tap water is subjected to electrolysis under conditions that the bromide ion and chloride ion coexist therein, the electrolytically-generated water exhibits an oxidizing capability which is higher than that of electrolytically-generated water in which only one of bromide ion and chloride ion exists. Thus, the sterilizing and washing processing can be performed not only in a shorter time but also at a less expensive cost by the mixed use of expensive bromide such as sodium bromide, etc. for supplying bromide ion and less expensive chloride such as sodium chloride, etc. for supplying chloride ion as compared with the case that only bromide ion is used.

In the medical instrument sterilizing and washing method according to the present invention, it is preferable that the ratio of the chloride ion and the bromide ion is suitably adjusted in order to increase the ratio of the chloride ion when the hydrogen ion concentration in the electrolytically-generated water is low and increase the ratio of the bromide ion when the hydrogen ion concentration therein is high.

With this arrangement, since the amount of bromide to be used can be minimized by changing the ratio of bromide ion and chloride ion based on the hydrogen ion concentration (pH) of the electrolytically-generated water, the cost of the sterilizing and washing processing can be reduced as well as when the pH of the electrolytically-generated water increases, the drop of the washing and sterilizing capability below a specific capability can be prevented by increasing the ratio of the bromide ion, whereby stable sterilizing and washing processing can be realized.

In the medical instrument sterilizing and washing method according to the present invention, it is preferable that the hydrogen ion concentration is maintained to 6–8 by adding an alkali material containing hydrogen ion when the pH in the electrolytically-generated water decreases to 6 or less and adding inorganic acid containing hydrogen ion when the pH increases to 8 or more.

With this arrangement, even if the hydrogen ion concentration (pH) of the electrolytically-generated water is changed by the materials deposited on the medical instrument to be sterilized and washed, since the pH is maintained to 6–8, the metal of the medical instrument is not corroded by the drop of the pH. Further, since the existing ratio of hypobromous acid generated by the electrolysis is very high in the pH set to 6–8, a high sterilizing and washing capability can be obtained and the sterilizing and washing processing can be stably carried out in a shorter time.

In the medical instrument sterilizing and washing method according to the present invention, it is preferable that the electrolytically-generated water is contacted with the medical instrument at a temperature of at least 30° C.

With this arrangement, since the oxidation reaction force of the hypohalogenous acid generated by the electrolysis can be increased, a higher sterilizing and washing capability can be obtained and, as a result, the sterilizing and washing processing can be executed in a shorter time.

In the medical instrument sterilizing and washing method according to the present invention, it is preferable to determine that sterilizing and washing processing has been completed when the concentration of the hypohalogenous acid contained in the electrolytically-generated water which is in contact with the medical instrument is detected and the hypohalogenous acid concentration maintains a value equal to or larger than a specific value for a specific period of time.

With this arrangement, when the sterilizing and washing processing is sufficiently carried out, since the amount of the hypohalogenous acid consumed in the sterilizing and washing processing is reduced and the concentration of the hypohalogenous acid in the electrolytically-generated water in contact with a medical instrument is increased, it can be found when necessary that the medical instrument has been perfectly sterilized and washed, whereby it can be prevented that the medical instrument is imperfectly sterilized and washed.

A medical instrument sterilizing and washing apparatus according to the present invention comprises a circulation passage for sterilizing and washing water in which a halide is dissolved; a medical instrument sterilizing and washing unit disposed at an arbitrary position in the circulation passage; a pump unit for forcibly circulating the sterilizing and washing water; an electrolytically-water-generating unit for causing the sterilizing and washing water to pass between an anode and a cathode in the circulation passage and subjecting the sterilizing and washing water to electrolysis; pH detection means for detecting the hydrogen ion concentration (pH) in the sterilizing and washing water; and pH maintenance means for maintaining the hydrogen ion concentration (pH) detected by the pH detection means to 6–8.

According to the above feature, since pH in the sterilizing and washing water is maintained to 6–8 at all times, the sterilizing and washing processing can be carried out without corroding the metal and the like of the medical instrument.

In the medical instrument sterilizing and washing apparatus according to the present invention, it is preferable that the halide is composed of a bromine component as a simple substance or a bromide compound and other halogenated compound.

With this arrangement, since the existence ratio of the hypobromous acid generated by the electrolysis is very high in the region of pH of 6–8, a high sterilizing and washing capability can be obtained by the strong oxidizing capability resulting from the hypobromous acid.

A medical instrument sterilizing and washing apparatus according to the present invention comprises a circulation passage for sterilizing and washing water in which a halide is dissolved; a medical instrument sterilizing and washing unit disposed at an arbitrary position in the circulation passage; a pump unit for forcibly circulating the sterilizing and washing water; an electrolytically-water-generating unit for causing the sterilizing and washing water to pass between an anode and a cathode in the circulation passage and subjecting the sterilizing and washing water to electrolysis; pH detection means for detecting the hydrogen ion concentration (pH) in the sterilizing and washing water; and ratio adjustment means for changing the ratio of chloride and bromide to be dissolved in the sterilizing and washing water based on the hydrogen ion concentration (pH) detected by the pH detection means.

According to the above feature, a higher sterilizing and washing capability can be obtained by subjecting to electrolysis the sterilizing and washing water in which chloride and bromide are dissolved, as compared with the case where only one of chloride and bromide is used. In addition, since expensive bromide such as sodium bromide, etc. and less expensive chloride such as sodium chloride, etc. are used in a mixed state, the sterilizing and washing processing can be carried out at a cost lower than that when bromide is used alone.

Further, since the amount of bromide to be used can be minimized by changing the ratio of bromide and chloride based on the hydrogen ion concentration (pH) in the sterilizing and washing water so that the ratio of the chloride is increased when the pH is low and the ratio of the bromide is increased when the pH is high, the amount of the bromide to be used can be minimized. As a result, the cost of the sterilizing and washing processing can be reduced as well as when the pH of the electrolytic water increases, the drop of the washing and sterilizing capability below a specific capability can be prevented by increasing the ratio of the bromine ion, whereby stable sterilizing and washing processing can be realized.

The medical instrument sterilizing and washing apparatus according to the present invention preferably comprises temperature increasing means located at a specific position in the circulation passage for increasing the temperature of the sterilizing and washing water to at least 30°.

With this arrangement, since the oxidation reacting force of the hypohalogenous acid generated by the electrolysis can be increased, a higher sterilizing and washing capability can be obtained and the sterilizing and washing processing can be executed in a shorter time.

The medical instrument sterilizing and washing apparatus of the present invention preferably comprises voltage measurement means for measuring an electric potential difference arisen when a constant current flows between the respective electrode plates of the electrolytically-water-generating unit and a dissolving amount control means for making the electric potential difference to a specific electric potential difference by controlling the amount of the halide to be added to and dissolved in the sterilizing and washing water.

With this arrangement, since the electric conductivity of the sterilizing and washing water can be maintained at a substantially constant level, not only hypohalogenous acid can be stably generated by the electrolysis but also the deterioration of the electrodes can be prevented and the life thereof can be prolonged by suppressing the increase of a voltage imposed across the electrode plates of the electrolytically-water-generating unit.

The medical instrument sterilizing and washing apparatus according to the present invention preferably comprises hypohalogenous acid detection means disposed at a specific position in the circulation passage for detecting the concentration of the hypohalogenous acid contained in the sterilizing and washing water; timer means for measuring a specific period of time; and determination means and/or notification means for determining that sterilizing and washing processing has been completed when a specific hypohalogenous acid concentration is detected for a specific period of time at the specific position.

With this arrangement, when the sterilizing and washing processing is sufficiently carried out, since the amount of the hypohalogenous acid consumed in the sterilizing and washing processing is reduced and the concentration of the hypohalogenous acid in the sterilizing and washing water in contact with a medical instrument is increased, it can be found when necessary that the medical instrument has been perfectly sterilized and washed and this condition can be notified to the operator, whereby it can be prevented that the medical instrument is imperfectly sterilized and washed.

In the medical instrument sterilizing and washing apparatus according to the present invention, it is preferable that the medical instrument sterilizing and washing unit additionally comprises ultrasonic wave generation unit for generating an ultrasonic wave and/or vibration means for applying vibration to the sterilizing and washing water.

With this arrangement, since the molecular motion in the sterilizing and washing water is increased by the application of an ultrasonic wave to the sterilizing and washing water, the oxidation reaction force of the hypohalogenous acid generated by the electrolysis can be increased just as in the case where the temperature of the sterilizing and washing water is increased. In addition, the washing capability of the sterilizing and washing water can be also increased by the water flow caused by the ultrasonic wave.

Further, the washing effect can be increased for a medical instrument and the like formed in a tube-shape such as an endoscope and the like by applying vibration thereto.

The medical instrument sterilizing and washing apparatus according to the present invention preferably comprises at least one filter disposed at a specific position in the circulation passage for capturing undissolved foreign material contained in the circulating sterilizing and washing water.

With this arrangement, flesh pieces and fine germs existing in the circulating sterilizing and washing water are captured and the hypohalogenous acid contained in the sterilizing and washing water comes into effective contact with the flesh pieces and fine germs as well as the hypohalogenous acid comes into contact with the filter to thereby generate free radicals having high oxidation reactivity. As a result, the reaction to the flesh pieces and fine germs is accelerated, whereby a higher sterilizing and washing effect can be obtained and further the sterilizing and washing water can be maintained in a sterile condition at all times.

DESCRIPTION OF THE PREFERRED EMBODIMENT

Embodiments of the present invention will be described below with reference to the accompanying drawings.

Figure 1:
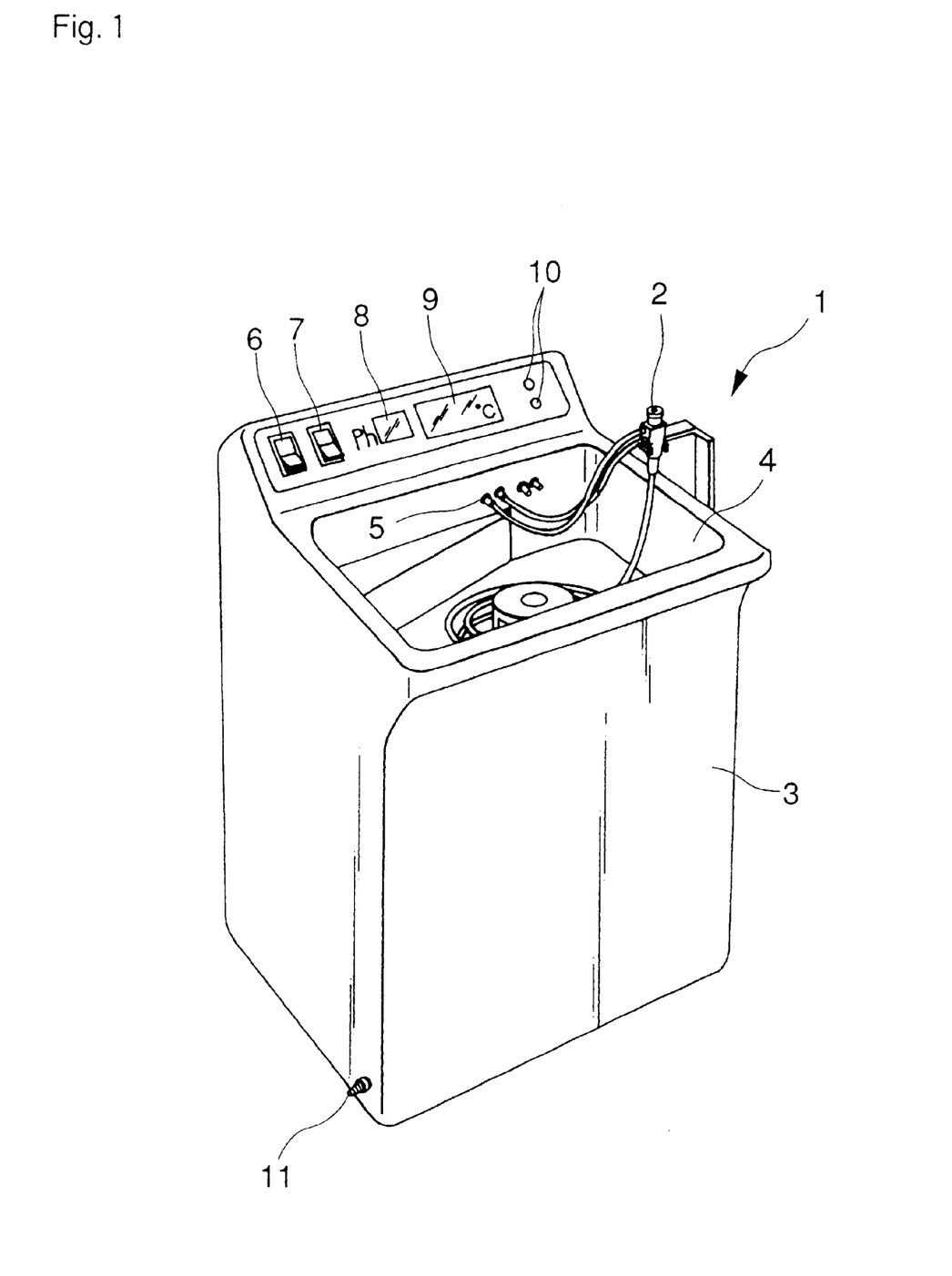
FIG. 1 is an outward appearance perspective view showing an endoscope sterilizing and washing apparatus according to an embodiment of the present invention.
Figure 2:
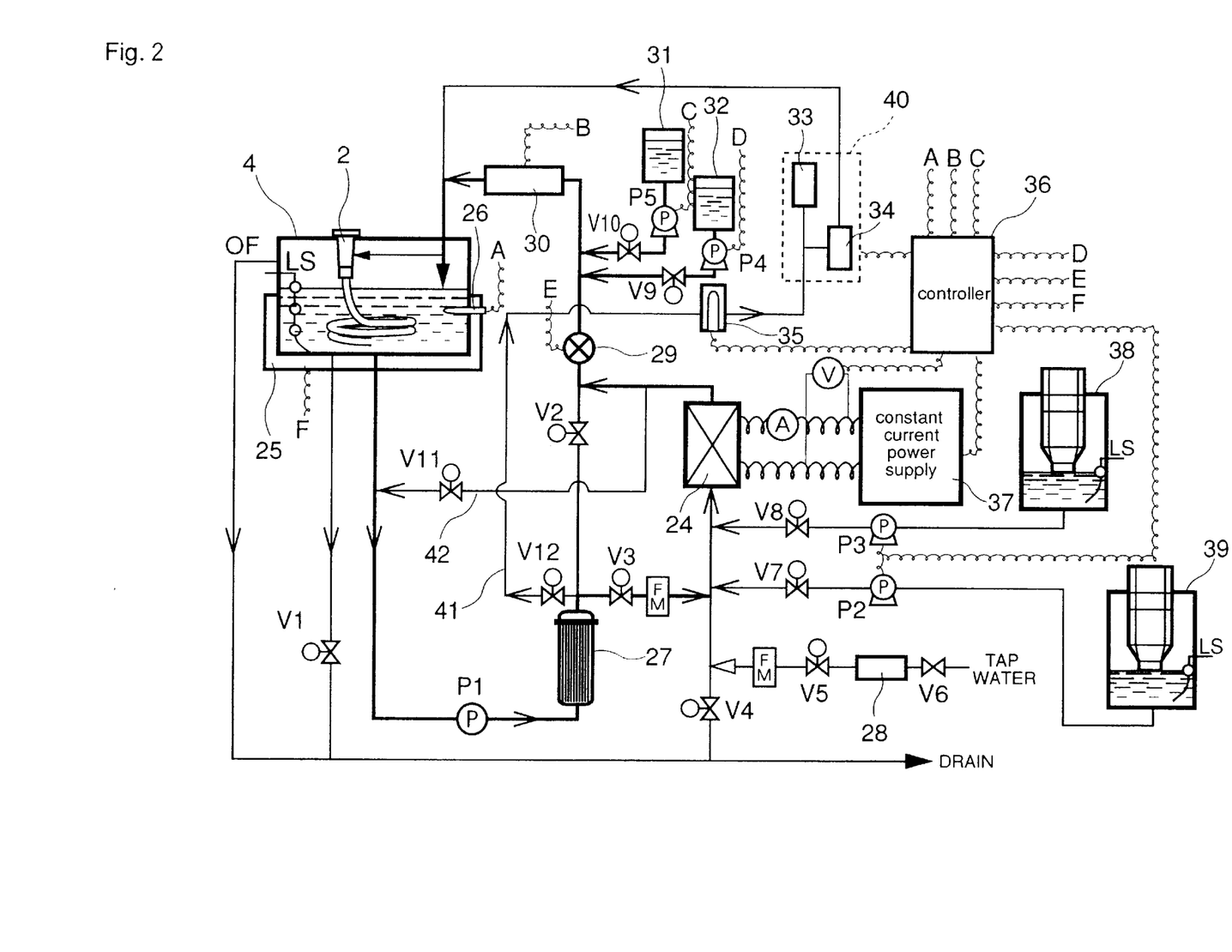
FIG. 2 is a system flowchart showing the arrangement of the endoscope sterilizing and washing apparatus according to the embodiment of the present invention.
Figure 3:
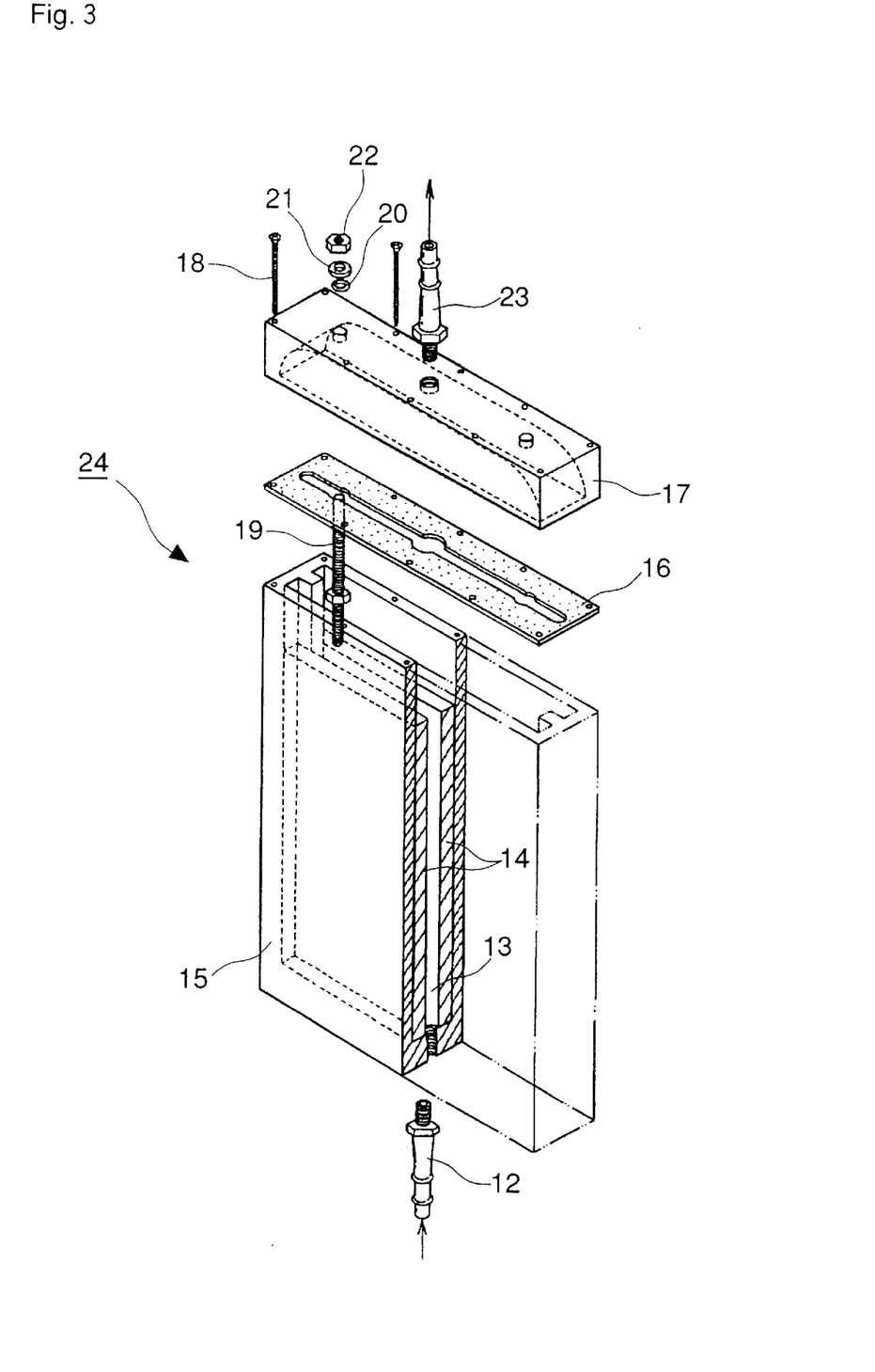
FIG. 3 is an exploded perspective view, partly in cross section, showing the structure of an electrolyzing device used in the endoscope sterilizing and washing apparatus according to the embodiment of the present invention.

FIG. 1 is an outward appearance perspective view showing a medical instrument sterilizing and washing apparatus according to an embodiment, FIG. 2 is a system flowchart showing the arrangement of the medical instrument sterilizing and washing apparatus according to the embodiment and FIG. 3 is an exploded perspective view, partly in cross section, showing the structure of an electrolysis reaction device used in the medical instrument sterilizing and washing apparatus according to the embodiment. In FIG. 2, LS denotes level sensors for measuring a water level, FM denotes flow meters, P denotes pumps and V denotes valves.

In the embodiment, the present invention is applied to an apparatus for sterilizing and washing an endoscope as a medical instrument.

As shown in FIG. 1, a sterilizing and washing apparatus 1 for endoscope as medical instrument (hereinafter, abbreviated as a sterilizing and washing apparatus) of the embodiment has an outward appearance approximately similar to that of a prior art endoscope sterilizing and washing apparatus. The sterilizing and washing apparatus 1 is provided with a sterilizing and washing vessel 4 for sterilizing and washing an endoscope 2 held in the upper surface portion of a main body 3 with sterilizing and washing water stored in the vessel 4, the sterilizing and washing vessel 4 has a guide disposed therein around which the far end of the endoscope 2 formed in a long string-shape is wound and a discharge plug 5 is disposed in a side wall of the sterilizing and washing vessel 4 to supply the sterilizing and washing water into the endoscope 2.

An operation panel is disposed in the upper portion of the main body 3 and includes a main switch 6, an ultrasonic operation switch 7, a pH display unit 8 for displaying the pH of the sterilizing and washing water, a temperature display unit 9 for displaying the temperature of the sterilizing and washing water and a display lamp 10 for notifying that sterilizing and washing processing has been finished to the operator.

The interior of the main body of the sterilizing and washing apparatus 1 of the embodiment is arranged as shown in FIG. 2. That is, mainly disposed therein are the sterilizing and washing vessel 4 as a medical instrument sterilizing and washing unit for storing the sterilizing and washing water and causing it to come into contact with the endoscope 2 for sterilizing and washing it, a circulation pump PI as a pump unit for forcibly circulating the sterilizing and washing water from the lower portion of the sterilizing and washing vessel 4 to a circulation passage, a filter 27 for eliminating undissolved foreign matters resulting from the oxidizing reaction in the sterilizing and washing water, a constant flow valve 28 for maintaining the flow amount of tap water to be supplied constant, a sodium chloride aqueous solution tank 39 for storing a sodium chloride aqueous solution set to a specific concentration to supply chloride ion to the sterilizing and washing water, a sodium bromide aqueous solution tank 38 for storing a sodium bromide aqueous solution set to a specific concentration to supply bromide ion to the sterilizing and washing water, an electrolytic device 24 for generating electrolytic water by electrolyzing the sterilizing and washing water, a constant current power supply for supplying a specific constant current to the electrolytic device 24, a flow switch 29 for controlling the circulation of the sterilizing and washing water, a temperature sensor 26 for detecting the temperature of the sterilizing and washing water in the sterilizing and washing vessel 4, a heater 30 for increasing the temperature of the sterilizing and washing water to a specific temperature based on the temperature detected by the temperature sensor 26, a pH sensor 35 for detecting the hydrogen ion concentration of the sterilizing and washing water, an acid tank 31 for storing sulfuric acid having a specific concentration and an alkali tank 32 for storing a sodium hydroxide aqueous solution having a specific concentration to adjust the pH value of the sterilizing and washing water based on the pH value detected by the pH sensor 35, a residual halogen concentration detecting unit 40 composed of a reference electrode 33 and a measuring electrode 34 to measure the residual halogen concentration of the sterilizing and washing water, an ultrasonic generator 25 for applying an ultrasonic wave to the sterilizing and washing water in the sterilizing and washing vessel 4 and a controller 36 connected to the respective units to control them, wherein the respective units are connected to each other through the circulation passage as shown in FIG. 2 and the sterilizing and washing water containing hypohalogenous acid which is generated by the electrolytic device 24 is supplied to the sterilizing and washing vessel 4 and the interior of the endoscope 2 to sterilize and wash the endoscope 2.

In FIG. 2, all the valves except a valve V6 are composed of an electromagnetic valve and connected, although not shown, to the controller 36 so that they are suitably opened and closed by being controlled by it.

Since the filter 27 used in the present invention comes into contact with the sterilizing and washing water containing the hypohalogenous acid which has a high oxidizing capability, it is preferable that the filter 27 is composed of a high-polymer material having high resistance to oxidation. Although poly(vinylpyrrolidone), polysulfone, etc. are exemplified as the high-polymer material of the filter 27, the material is not limited thereto and a filter device using active carbon, rock and the like may be used. The filter 27 is preferably used to purify the sterilizing and washing water by accelerating the oxidizing reaction of it in the filter.

The electrolytic device 24 used in the embodiment is arranged as shown in FIG. 3 and has an electrolysis passage 13 formed between two electrode plates 14 to perform electrolysis.

The electrode plates 14 are composed of a ferrite plate as an anode and a titanium plate as a cathode and the respective electrode plates 14 are disposed by being inserted into a cabinet 15 of polyvinyl chloride which is formed to a shape for providing a specific spacing between the electrode plates 14.

The spacing between the electrode plates 14 is within the range of 1–10 mm and preferably the range of 3–6 mm and set to 6 mm in the embodiment.

The cabinet 15 has an opening at an end thereof which is covered with a lid member 17 of polyvinyl chloride secured thereto by flat head screws 18 through a packing 16. The electrode plates 14 include electrode terminals 19 (only one of them is shown) which are exposed to the outside of the cabinet 15 through the lid member 17 and each of the electrode terminals 19 is secured to the lid member 17 by an O-ring 20, a round washer 21 and a stainless steel nut 22. A direct current is supplied to the electrode terminals 19 from a rectified power supply, an inlet joint 12 and an outlet joint 23 which communicate with the electrolysis passage 13 are formed to both the ends of the electrolyzing device 24 so as to supply the sterilizing and washing water which circulates from below the electrolytic device 24.

The constant current power supply 37 supplies a specific constant current (which is set to 10A in the embodiment) between the electrode plates 14 disposed on both the sides of the electrolysis passage 13 in the electrolytic device 24. When it is supposed that the area of the electrode plates 14 is 2 $dm^2$ and the electric conductivity of the sterilizing and washing water is 1000–2000 $\mu s/cm$ as a specific value, a voltage of 6.0–6.2 V is generated between the electrode plates 14. Thus, the voltage between the electrode plates 14 is measured by a voltmeter and the amounts of the sodium bromide aqueous solution and the sodium chloride aqueous solution supplied from the sodium bromide aqueous solution tank 38 and the sodium chloride aqueous solution tank 39 are controlled by the controller 36 through metering pumps P3 and P2.

Operation of the sterilizing and washing apparatus 1 of the embodiment will be described. In operation, magnetic valves V1, V4 connected to a drain are normally closed and the valve V6 is opened first to thereby supply tap water into the circulation passage and the sterilizing and washing vessel 4 through the constant flow valve 28 and an electromagnetic valve V5.

The thus supplied tap water is suitably added with the sodium bromide aqueous solution and the sodium chloride aqueous solution as an electrolyte from the sodium bromide aqueous solution tank 38 and the sodium chloride aqueous solution tank 39 by the metering pumps P2 and P3 when necessary so that the electric conductivity of the sterilizing and washing water is adjusted so as to impose a specific voltage on the electrodes of the electrolytic device 24 while the tap water circulates through the circulation passage.

The tap water being supplied to the circulation passage and the sterilizing and washing vessel 4 is stopped when the specific electric conductivity thereof is achieved and subjected to electrolysis in the electrolytic device 24 and made to the sterilizing and washing water in which both hypobromous acid and hypochlorous acid as hypohalogenous acid are generated. The temperature of the sterilizing and washing water is increased by the heater 30 until the temperature thereof detected by the temperature sensor 26 projecting into the sterilizing and washing vessel 4 achieves a specific temperature (it can be set in the embodiment) and then the sterilizing and washing water is returned to the sterilizing and washing vessel 4. The temperature detected by the temperature sensor 26 is displayed on the temperature display unit 9 of the operation panel by the controller 36.

A portion of the circulating sterilizing and washing water is diverted to a branch passage 41 downstream of the filter 27, the hydrogen ion concentration (pH) of the sterilizing and washing water is detected and measured by the pH sensor 35 disposed in the branch passage 41 and output to the controller 36 as well as the concentration of the hypohalogenous acid in the sterilizing and washing water is detected and measured by the residual halogen concentration detecting unit 40 and output to the controller 36. The thus detected hydrogen ion concentration (pH) is displayed on the pH display unit 8 of the operation panel.

The controller 36 suitably adds the sulfuric acid or the sodium hydroxide aqueous solution to the sterilizing and washing water by metering pumps P4, P5 connected to the acid tank 31 and the alkali tank 32 based on the pH value of the sterilizing and washing water detected and measured by the pH sensor 35 so as to maintain the pH value of the sterilizing and washing water to 6–8.

After the specific temperature, the specific pH value and the specific hypohalogenous acid concentration are achieved for the sterilizing and washing water, the circulation of the sterilizing and washing water is stopped by closing the flow switch 29, the endoscope 2 is placed into the sterilizing and washing vessel 4 and the flow switch 29 is opened again to resume the circulation of the sterilizing and washing water to thereby perform sterilizing and washing processing.

At this time, the ultrasonic operation switch 7 is turned on when necessary to apply an ultrasonic wave to the sterilizing and washing vessel 4.

When the sterilizing and washing processing starts, the hypohalogeneous acid is consumed by the blood, body fluid, germs, viruses, etc. deposited on the endoscope 2 and the hypohalogeneous acid concentration in the circulating sterilizing and washing water is lowered. When, however, the consumption of the hypohalogenous acid is reduced by the progress of the sterilizing and washing processing, the hypohalogeneous acid concentration of the circulating sterilizing and washing water is restored to the specific value.

The controller 36 is programmed such that after a period of time has elapsed as measured by a timer (not shown) disposed in the controller 36 the hypohalogeneous acid concentration of the circulating sterilizing and washing water is restored again to the specific value and it is determined that the sterilizing and washing processing has been sufficiently performed when a specific period of time elapses and the completion of the sterilizing and washing processing is notified to the operator by the display lamp 10 disposed to the upper portion of the main body 3 of the sterilizing and washing apparatus 1.

As shown in FIG. 2, a bypass passage is disposed downstream of the electrolytic device 24 to return a portion of the electrolyzed sterilizing and washing containing the hypohalogeneous acid upstream of the circulation pump P1 and the filter 27 can be suitably purified by the sterilizing and washing water containing the hypohalogeneous acid and supplied thereto.

Figure 4:
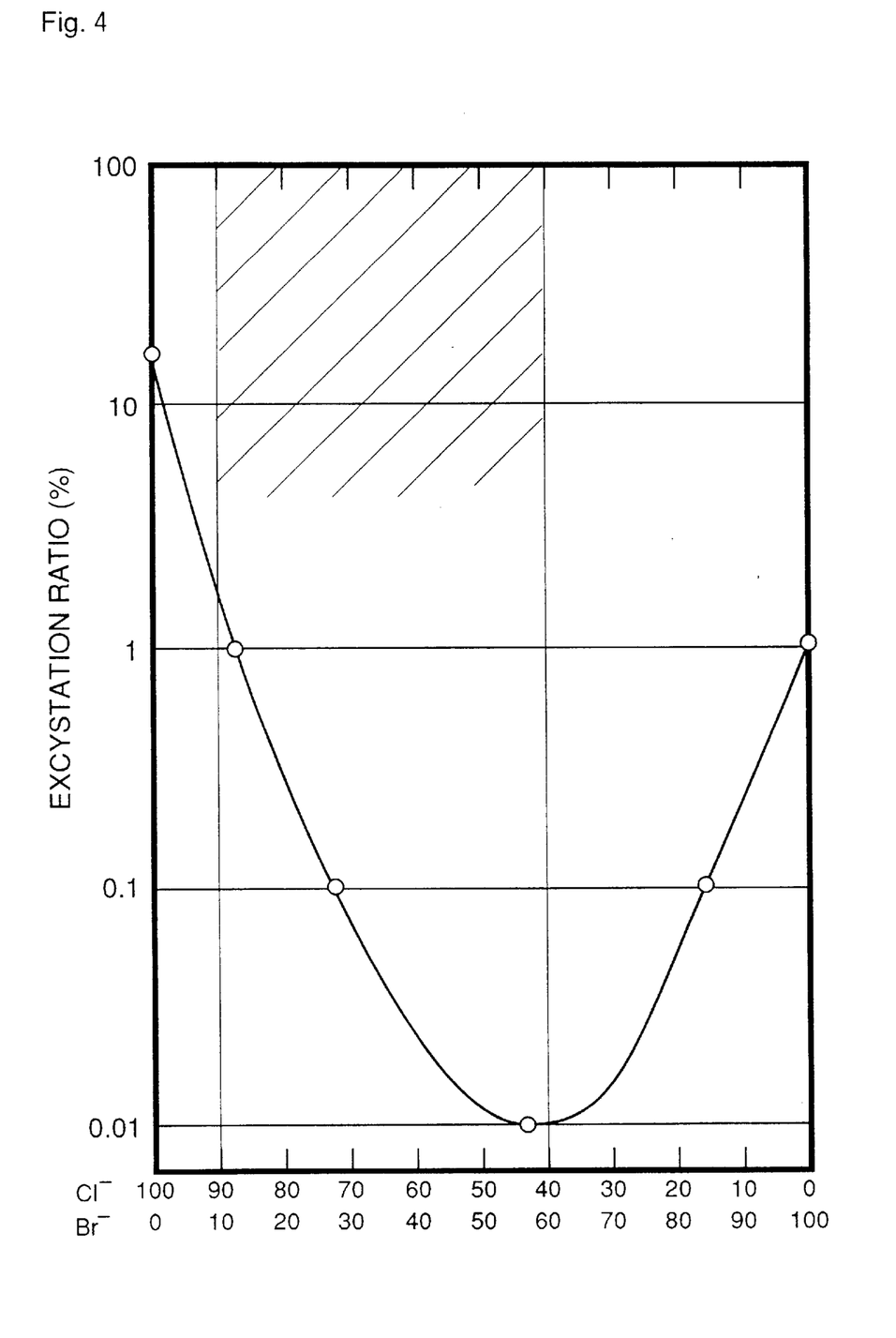
FIG. 4 is a graph showing how the excision ratio of Cryptosporidium changes when the mixing ratio of a sodium chloride aqueous solution and a sodium bromide aqueous solution is changed.

To compare the sterilizing power of the sterilizing and washing apparatus 1 described above with that of a prior art sterilizing and washing apparatus using sodium chloride alone as chloride, Cryptosporidium as resistance protozoans was added to the circulating sterilizing and washing water so that it had a specific concentration, a processing time was set to 30 minutes and sterilizing and washing processing was performed by changing the ratio of the sodium chloride aqueous solution and the sodium bromide aqueous solution supplied from the sodium chloride aqueous solution tank 39 and the sodium bromide aqueous solution tank 38. FIG. 4 shows the result of the above experiment.

At the time, the processing was carried out without heating the sterilizing and washing water and without applying an ultrasonic wave thereto.

A reason why Cryptosporidium was used to evaluate the sterilizing power is that since Cryptosporidium exhibits strong resistance to various sterilizing methods, it is considered that a sterilizing method capable of sterilizing Cryptosporidium has sufficient sterilizing power to many other germs.

In FIG. 4, excision means the condition that the oocyst wall of Cryptosporidium opens and sporozoite acting as a source of infection is discharged therefrom, an excision ratio is a value represented by a percentage which shows the Cryptosporidium in an excision state counted under a microscope when the initial state of the Cryptosporidium is represented by 100% and the value nearer to 0% indicates a better sterilized state.

It is found from the result shown in FIG. 4 that the processing performed using bromide ion alone which is supplied by bromide such as sodium bromide, etc. can achieve a higher sterilizing power as compared with a prior art processing performed using chloride ion of sodium chloride alone in the region where the pH of the sterilizing and washing water is maintained to 6–8 as in the sterilizing and washing apparatus 1 of the embodiment as well as a higher sterilizing power can be obtained by the coexistence of bromide ion and chloride ion as compared with the case in which only bromide ion is used.

As to the mixing mole ratio of chloride ion and bromide ion, sterilizing power of chloride ion and bromide ion which is substantially similar to that in which only bromide ion is used can be obtained in the presence of bromide ion:chloride ion is 1:9 in FIG. 4 and the sterilizing power of them is maximized in the presence of bromide ion:chloride ion is 6:4. In the region shown by slanted lines which is located between both the ratios, since the ratio of the chloride ion which can be supplied by less expensive sodium chloride is relatively high, a high sterilizing power can be obtained while suppressing the cost of the electrolyte to be added to the sterilizing and washing water. Thus, it is preferable to set the mixing mole ratio of chloride ion and bromide ion to the range of 9:1 to 4:6.

Since sterilizing power to other germs and the like was indistinct from the evaluation of the sterilization power made using Cryptosporidium, sterilizing power to hay germ spores was evaluated by the following evaluation method.

The evaluation method is such that germ liquids of 1 ml containing the spores in the amount of $1 \times 10^7$ spores/ml were put into test tubes, the sterilizing and washing water (hypohalogeneous acid concentration: 300 ppm and 500 ppm) prepared as described above by the sterilizing and washing apparatus 1 of the embodiment was added to the germ liquids so that they became 10 ml (spore concentration: 1×10⁶ spores/ml), the test tubes were heated to 20° C. and 40° C. for 15 minutes by a hot water of a specific temperature, the resulting solutions were diluted to 10 times, 100 times and 1000 times, respectively, the respective diluted solutions of 0.5 ml were added to soybean kasein digesting agar culture regions and cultured at 35° C. for 48 hours, the numbers of the colonies at the respective test culture regions were counted three times, and then the average value of the numbers of the colonies was determined. The result of the evaluation is as described below.

TABLE 1

| MOLE RATIO | | PROCESSING TEMPERATURE 20° C. | | PROCESSING TEMPERATURE 40° C. | |
|---|---|---|---|---|---|
| Br⁻ | Cl⁻ | 300 ppm | 500 ppm | 300 ppm | 500 ppm |
| 100 | 0 | 96 | 5.8 | 21 | 2 |
| 77 | 23 | 12 | 0.26* | 3.1 | 0.15* |
| 57 | 43 | 8 | 0.05* | 1.5 | 0* |
| 35 | 65 | 13 | 0.22* | 1.8 | 0.11* |
| 10 | 90 | 98 | 2.6 | 12 | 0.45* |
| 0 | 100 | 1200 | 21 | 150 | 3.1 |

*SHOWN BY AVERAGE VALUE AS IT IS ALTHOUGH THE VALUE IS INTRINSICALLY "0"

Figure 5:
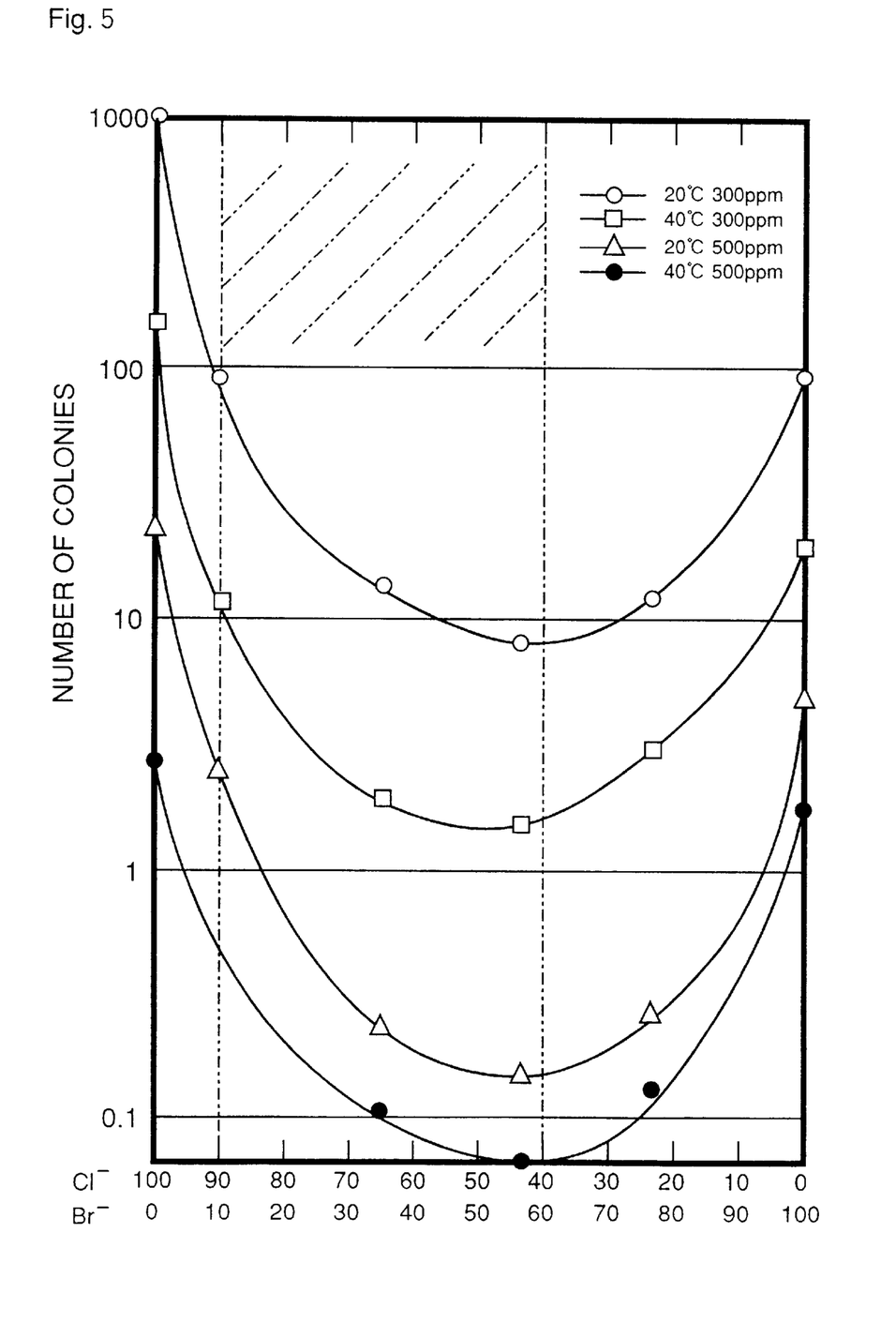
FIG. 5 is a graph showing the number of colonies of hay germ spores under respective conditions when the mixing ratio of sodium chloride aqueous solution and sodium bromide aqueous solution is changed in the embodiment of the present invention.

FIG. 5 is a graph showing the result of the above experiment so as to make it understandable. It is found from the result that the sterilizing and washing water prepared by the sterilizing and washing apparatus 1 of the embodiment also has a very strong sterilizing effect to the hay germ spores as well as when bromide ions are mixed with chloride ion as in the the case of the above Cryptosporidium, they have a sterilizing power higher than that achieved when only bromide ion is used in a mole ratio approximately between 6:4 and 1:9.

It can be also found that the increase of the temperature in the processing can increase sterilizing effect.

Figure 6:
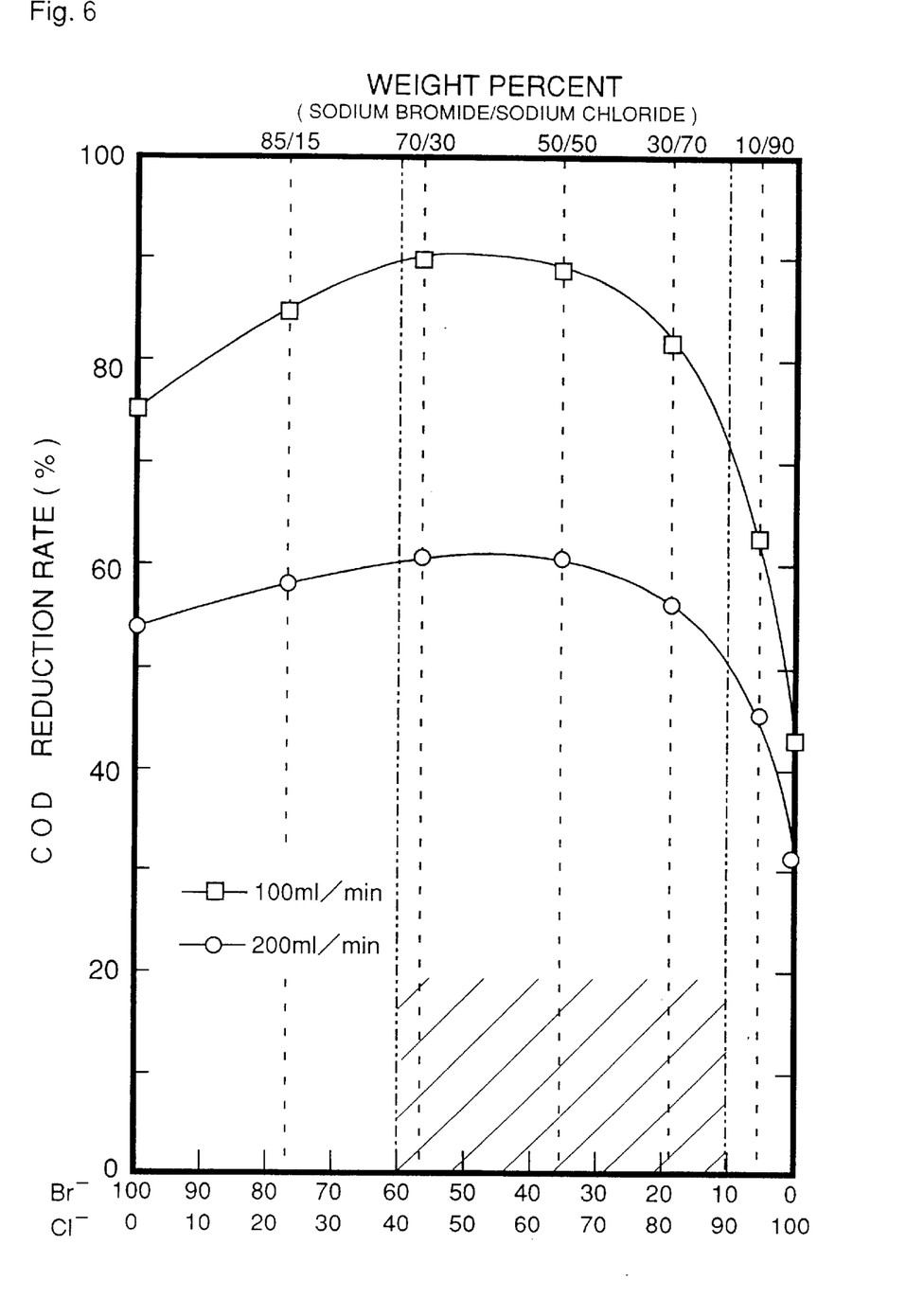
FIG. 6 is a graph showing how a COD reduction ratio is changed when the mixing ratio of sodium chloride aqueous solution and sodium bromide aqueous solution is changed in the embodiment of the present invention.

Next, to compare the washing capability of the sterilizing and washing apparatus 1 for a body fluid, blood and the like with that of a prior art apparatus which uses only sodium chloride as chloride, an organic dirty component corresponding to the dirt such as a body liquid, blood and the like was added to the circulating sterilizing and washing water so that it became a specific COD value (about 10 mg/l) and processing was executed by causing the sterilizing and washing water to pass through the electrolytic device 24 at flow rates of 100 ml/min. and 200 ml/min. while changing the ratio of the sodium chloride aqueous solution and the sodium bromide aqueous solution supplied from the sodium chloride aqueous solution tank 39 and the sodium bromide aqueous solution tank 38. FIG. 6 shows the result of the above processing.

At the time, the processing was carried out without heating the sterilizing and washing water by the heater 30 and without applying an ultrasonic wave thereto.

In FIG. 6, a COD reduction ratio is obtained by dividing the reduced amount of the COD value in the sterilizing and washing water which is reduced by the oxidizing power of the hypohalogeneous acid generated by the electrolytic device 24 by the COD value in the sterilizing and washing water before the processing is carried out and a higher value of the COD reduction ratio indicates a higher purifying capability.

As shown in FIG. 6, it is found that the hypobromous acid made from bromide ion supplied by a sodium bromide aqueous solution is superior to the hypochlorous acid made from chloride ion supplied by a sodium chloride aqueous solution in a washing processing capability when they are used as a simple substance as well as it is also found that the washing processing capability can be made higher when chloride ion and bromide ion coexist in the sterilizing and washing water than when only bromide ion or chloride ion exists therein.

As to the mixing mole ratio of chloride ion and bromide ion, washing processing capability of chloride ion and bromide ion which is substantially similar to that in which only bromide ion is used can be obtained in the presence of bromide ion:chloride ion is 1:9 in FIG. 6 as in the case where the sterilizing power and the washing processing capability of them is maximized in the presence of bromide ion:chloride ion is 6:4. In the region shown by slanted lines which is located between both the ratios, since the ratio of the chloride ion which can be supplied by less expensive sodium chloride is relatively high, a high washing processing capability can be obtained while suppressing the cost of an electrolyte which will be added to the sterilizing and washing water. Thus, it is preferable to set the mixing mole ratio of bromide ion and the chloride ion to the range of 1:9 to 6:4.

Although the sterilizing and washing capability is greatly improved when a small amount of bromide ion is added to chloride ion, a reason of which will be described below.

Figure 8:
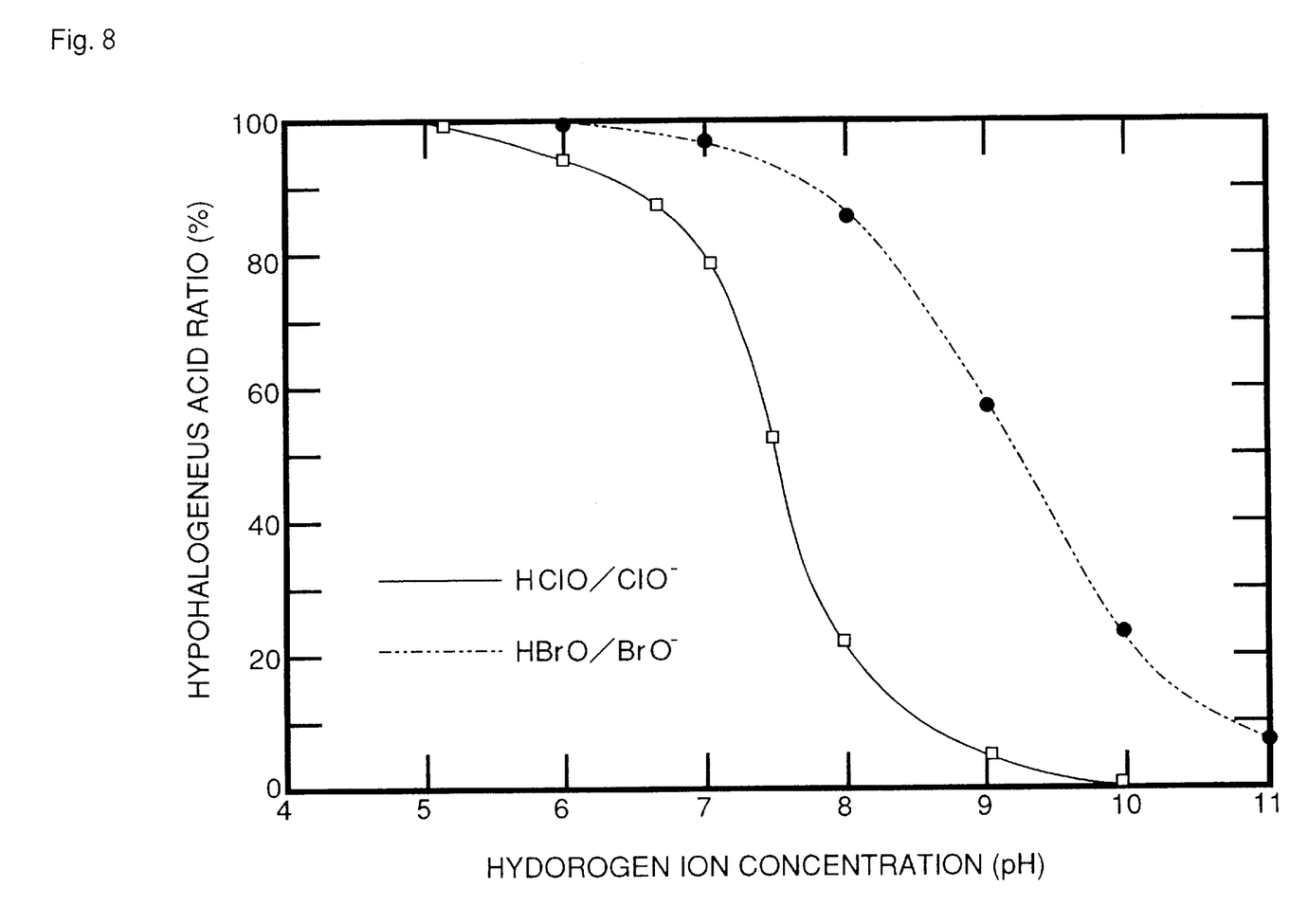
FIG. 8 is a graph showing the relationship between the existing ratio of hypochlorite acid and hypochlorous acid and hypobromite and hypobromous acid and hydrogen ion concentration (pH) when sodium chloride and sodium bromide are used as simple substances.

As shown in the following chemical formula, this is believed to result from an ion exchange being carried out between the hypobromous acid generated by the electrolysis and the bromide ion and the hypobromous acid is generated which can exist even in the neutral region of pH 6–8 at a relatively high ratio as shown in FIG. 8.

$HClO + Br^- \rightarrow HBrO + Cl^-$

Figure 7:
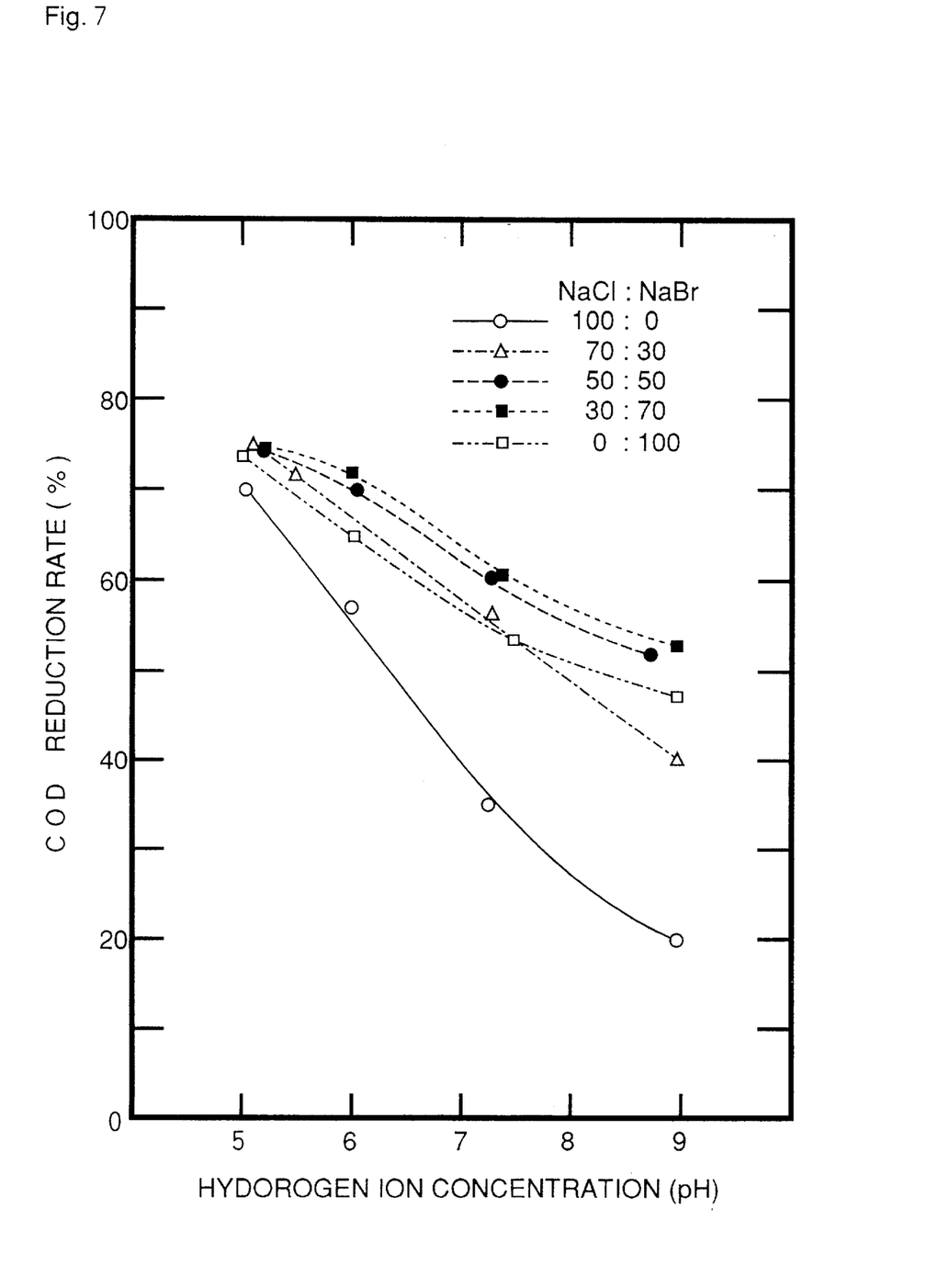
FIG. 7 is a graph showing the relationship between the COD reduction ratio and the respective mixing ratios of sodium chloride aqueous solution and sodium bromide aqueous solution at respective hydrogen ion concentrations (pH)

Since there was a possibility that the oxidizing capability was changed depending upon the hydrogen ion concentration (pH) of the sterilizing and washing water also in the hypobromous acid as well as the sterilizing and washing capability of the mixed system of the bromide ion and the chloride ion was greatly changed by the change of the hydrogen ion concentration (pH) which was caused by the mixture of the chloride ion as described above, the hydrogen ion concentration (pH) in the sterilizing and washing water which was set to the above COD value (about 10 mg/l) was changed to 5–9 by the addition of the sulfuric acid in the acid tank 31 or the sodium hydroxide aqueous solution in the alkali tank 32 and FIG. 7 shows the COD reduction ratio at the time.

As shown in FIG. 7, it is found that when the weight ratio of sodium bromide and sodium chloride is at least 3:7 (about 2:8 in mole ratio), substantially the same or a greater washing processing capability can be maintained up to the vicinity of pH 8. In addition, since stainless steel such as SUS 304 and the like used to form medical instruments is not corroded when the pH of the sterilizing and washing water is at least 6, the sterilizing and washing processing can be effectively carried out in a short time with a high sterilizing and washing capability without corroding the metal of the medical instruments by maintaining the pH of the sterilizing and washing water to 6–8 as shown by the embodiment.

It is preferable from the result shown in FIG. 7 to change the ratio of sodium chloride and sodium bromide in accordance with the change of the pH of the sterilizing and washing water because the washing processing capability is changed by the change of the oxidizing capability of the hypohalogeneous acid which is caused by the change of the pH of the sterilizing and washing water. When, for example, the pH of the sterilizing and washing water is low, it is preferable to reduce processing cost by reducing the ratio of expensive sodium bromide because sufficient sterilizing and washing capability can be obtained even if the ratio of the sodium bromide is lowered, whereas when the pH of the sterilizing and washing water is high, it is preferable to permit sterilizing and washing processing to be stably performed by preventing the reduction of the sterilizing and washing capability by increasing the ratio of the sodium bromide. Thus, it is preferable to change the ratio of sodium bromide and sodium chloride when necessary as executed in the embodiment.

Next, the sterilizing and washing water, which had a COD value of 28 mg/l and a total nitrogen component of about 35 mg/l, was caused to pass through the electrolytic device 24 at a flow rate of 150 ml/min. while supplying the sodium chloride aqueous solution and the sodium bromide aqueous solution to the sterilizing and washing water from the sodium chloride aqueous solution tank 39 and the sodium bromide aqueous solution tank 38 so that the ratio of sodium chloride and sodium bromide was set to 7:3. Thereafter, the COD reduction ratio of the sterilizing and washing water was measured as to the case that the heater 30 was operated to heat it to 30° and 50° and the case that the ultrasonic generator 25 was operated to apply an ultrasonic wave thereto. Table 2 shows the result of measurements.

TABLE 2

NaBr:NaCl = 3:7 (WT %)

| CONTENT OF PROCESSING | TEMP. (° C.) | pH | TOTAL NITROGEN (mg/l) | C O D (mg/l) | RESIDUAL BROMINE (mg/l) | RESIDUAL CHLORINE (mg/l) |
|---|---|---|---|---|---|---|
| UN-PROCESSING | 20 | 8.3 | 34.7 | 28.1 | 0 | 0.1 |
| WITHOUT HEATING WITHOUT ULTRA-SONIC WAVE | 21 | 7.3 | 7.6 | 9.8 | 73.2 | 32.5 |
| ONLY HEATING (30° C.) | 30 | 7.2 | 6.2 | 8.1 | 54.1 | 25.0 |
| ONLY HEATING (50° C.) | 50 | 7.1 | 2.5 | 4.2 | 28.4 | 14.1 |
| ONLY ULTRA-SONIC WAVE | 21 | 7.3 | 6.8 | 8.7 | 60.0 | 28.2 |
| HEATING (50° C.) + ULTRA-SONIC WAVE | 50 | 7.2 | 2.1 | 3.5 | 27.1 | 13.2 |

It is found from the result of measurements that the heating of or the application of the ultrasonic wave to the sterilizing and washing water greatly reduces both the amounts of the COD component and total nitrogen component in the sterilizing and washing water as compared with the sterilizing and washing water which is not heated or to which no ultrasonic wave is generated. It is also found that the simultaneous execution of the heating operation and the ultrasonic wave generation results in a higher washing capability.

A heating temperature may be suitably selected depending upon the heat resistance and the like of the sterilizing and washing apparatus 1, the electrolytic device 24 and the like and is not particularly limited. However, the temperature is preferably set to the range of 30° to 70° because a higher temperature requires a higher cost.

Although test pieces of SUS 304 were dipped in the sterilizing and washing vessel 4 in the above tests, none of them were rusted or corroded.

While the present invention has been described with reference to the accompanying drawings, it is by no means limited to the above embodiments and it goes without saying that various improvements and additions can be made within the range which does not depart from the gist of the present invention.

Although sodium chloride and sodium bromide are used as a halide in the respective embodiments, the present invention is not limited thereto and a halide of other alkali metal such as, for example, potassium, lithium, etc. and magnesium, calcium, etc. as alkaline earth metal may be used and they may be suitable selected depending upon the cost and the like of the halide.

Although sodium chloride and sodium bromide the specific aqueous solutions are added to tap water or circulating sterilizing and washing water after they are made to specific aqueous solutions, the present invention is not limited thereto and it is needless to say that the respective electrolytes may be directly added to and dissolved in the tap water or the circulating sterilizing and washing water.

Although the sterilizing and washing apparatus 1 of the embodiments is not provided with a mechanism and the like for stirring the sterilizing and washing water in the sterilizing and washing vessel 4 or creating a water flow in the vessel, the washing effect in the sterilizing and washing vessel 4 may be increased a time necessary to the sterilizing and washing processing may be reduced by the provision of the mechanism and the like.

The following advantages can be achieved by the present invention.

(a) According to the present invention, since the hypobromous acid as hypohalogenous acid generated by the electrolysis exists in the electrolytically-generated water at a high ratio even if the hydrogen ion concentration (pH) is at least 6, the contact of the electrolytically-generated water with the materials deposited to a medical instrument having been used can wash and sterilize organic stains, germs, viruses and the like deposited thereto by the strong oxidizing action of the hypohalogenous acid as well as the electrolytically-generated water does not corrode the metal and the like used to form the medical instrument because the hydrogen ion concentration (pH) thereof is at least 6.

(b) According to the present invention, since tap water is subjected to electrolysis under conditions in which the bromide ion and chloride ion coexist therein, the electrolytically-generated water exhibits an oxidizing capability which is higher than that of the electrolytically-generated water in which any one of bromide ion and chloride ion exists. Thus, the sterilizing and washing processing can be performed not only in a shorter time but also at a less expensive cost by the mixed use of expensive bromide such as sodium bromide, etc. for supplying bromide ion and less expensive chloride such as sodium chloride, etc. for supplying chloride ion as compared with the case that only bromide ion is used.

(c) According to the present invention, since the amount of bromide to be used can be minimized by changing the ratio of bromide ion and chloride ion based on the hydrogen ion concentration (pH) of the electrolytically-generated water, the cost of the sterilizing and washing processing can be reduced as well as when the pH of the electrolytically-generated water increases, the drop of the washing and sterilizing capability below a specific capability can be prevented by increasing the ratio of the bromide ion, whereby stable sterilizing and washing processing can be realized.

(d) According to the present invention, even if the hydrogen ion concentration (pH) of the electrolytically-generated water is changed by the materials deposited to a medical instrument to be sterilized and washed, since the pH is maintained at 6–8, the metal used to form the medical instrument is not corroded by the drop of the pH. Further, since the existing ratio of the hypobromous acid generated by the electrolysis is very high in the pH set to 6–8, high sterilizing and washing capability can be obtained and the sterilizing and washing processing can be stably carried out in a shorter time.

(e) According to the present invention, since the oxidation reaction force of the hypohalogenous acid generated by the electrolysis can be increased, higher sterilizing and washing capability can be obtained and, as a result, the sterilizing and washing processing can be executed in a shorter time.

(f) According to the present invention, when the sterilizing and washing processing is sufficiently carried out, since the amount of the hypohalogenous acid consumed in the sterilizing and washing processing is reduced and the concentration of the hypohalogenous acid in the electrolytically-generated water in contact with a medical instrument is increased, it can be found when necessary that the medical instrument has been perfectly sterilized and washed, whereby it can be prevented that the medical instrument is imperfectly sterilized and washed.

(g) According to the present invention, since the pH in the sterilizing and washing water is maintained to 6–8 at all times, the sterilizing and washing processing can be carried out without corroding the metal and the like used to form the medical instrument.

(h) According to the present invention, since the existence ratio of the hypobromous acid generated by the electrolysis is very high in the region of pH of 6–8, high sterilizing and washing capability can be obtained by the strong oxidizing capability resulting from the hypobromous acid.

(i) According to the present invention, higher sterilizing and washing capability can be obtained by subjecting to electrolysis the sterilizing and washing water in which chloride and bromide are dissolved, as compared with the case that any one of chloride and bromide is used. In addition, since expensive bromide such as sodium bromide, etc. and less expensive chloride such as sodium chloride, etc. are used in a mixed state, the sterilizing and washing processing can be carried out at a cost lower than that when bromide is used alone.

Further, since the amount of bromide to be used can be minimized by changing the ratio of bromide and chloride based on the hydrogen ion concentration (pH) in the sterilizing and washing water so that the ratio of the chloride is increased when the pH is low and the ratio of the bromide is increased when the pH is high, the amount of the bromide to be used can be minimized. As a result, the cost of the sterilizing and washing processing can be reduced as well as when the pH of the electrolytic water increases, the drop of the washing and sterilizing capability below a specific capability can be prevented by increasing the ratio of the bromine ion, whereby stable sterilizing and washing processing can be realized.

(j) According to the present invention of, since the oxidation reacting force of the hypohalogenous acid generated by the electrolysis can be increased, higher sterilizing and washing capability can be obtained and the sterilizing and washing processing can be executed in a shorter time.

(k) According to the present invention, since the electric conductivity of the sterilizing and washing water can be maintained to a substantially constant level, not only hypohalogenous acid can be stably generated by the electrolysis but also the deterioration of the electrodes can be prevented and the life thereof can be prolonged by suppressing the increase of a voltage imposed across the electrode plates of the electrolytically-water-generating unit.

(l) According to the present invention, when the sterilizing and washing processing is sufficiently carried out, since the amount of the hypohalogenous acid consumed in the sterilizing and washing processing is reduced and the concentration of the hypohalogenous acid in the sterilizing and washing water in contact with a medical instrument is increased, it can be found when necessary that the medical instrument has been perfectly sterilized and washed and this state can be notified to the operator, whereby it can be prevented that the medical instrument is imperfectly sterilized and washed.

(m) According to the present invention, since the molecular motion in the sterilizing and washing water is increased by the application of an ultrasonic wave to the sterilizing and washing water, the oxidation reaction force of the hypohalogenous acid generated by the electrolysis can be increased as in the case that the temperature of the sterilizing and washing water is increased. In addition, the washing capability of the sterilizing and washing water can be also increased by the water flow caused by the ultrasonic wave.

Further, washing effect can be increased to a medical instrument and the like formed to a tube-shape such as an endoscope and the like by applying vibration thereto.

(n) According to the present invention, flesh pieces and fine germs existing in the circulating sterilizing and washing water are captured and the hypohalogenous acid contained in the sterilizing and washing water comes into effective contact with the flesh pieces and fine germs as well as the hypohalogenous acid comes into contact with the filter to thereby generate free radicals having high oxidation reactivity. As a result, the reaction to the flesh pieces and fine germs is accelerated, whereby higher sterilizing and washing effect can be obtained and further the sterilizing and washing water can be maintained to a clean state at all times.

What is claimed is:

1. A medical instrument sterilizing and washing method, comprising the steps of:

preparing an electrolytic aqueous solution by adding and dissolving a halide composed of a bromine compound as a simple substance or a bromine compound and another halogenated compound to and in tap water;

directly subjecting the electrolytic aqueous solution to electrolysis by circulating said electrolytic aqueous solution through an electrolytic cell having electrode plates composed of an anode and a cathode, whereby to generate electrolytically-generated water containing hypohalogenous acid; and circulating said electrolytically generated water from said electrolytic cell through a wash unit;

sterilizing and washing a medical instrument by placing said instrument in said wash unit in contact with said electrolytically-generated water;

detecting the hydrogen ion concentration of the circulating electrolytically-generated water, and adjusting the hydrogen ion concentration of the electrolytic water to maintain a pH of at least 6 at all times;

detecting the concentration of the hypohalogenous acid contained in the electrolytically-generated water in a residual halogen concentration detecting unit; and continuing said sterilizing and washing until the detected residual halogen concentration achieves a value equal to or larger than a specific value for a specific period of time.

2. A medical instrument sterilizing and washing method according to claim 1, wherein the halogen ion supplied by the halide electrolyte is bromide ion and chloride ion and they are used in a mole ratio within the range of 6:4 to 1:9.

3. A medical instrument sterilizing and washing method according to claim 2, wherein the ratio of chloride ion and bromide ion is suitably adjusted in order to increase the ratio of chloride ion when the hydrogen ion concentration (pH) in the electrolytically-generated water is low and increase the ratio of bromide ion when the hydrogen ion concentration (pH) therein is high.

4. A medical instrument sterilizing and washing method according to claim 1, wherein the hydrogen ion concentration is maintained to 6–8 by adding an alkali material containing hydrogen ion when the hydrogen ion concentration (pH) in the electrolytically-generated water decreases to 6 or less and adding inorganic acid containing hydrogen ion when the hydrogen ion concentration (pH) increases to 8 or more.

5. A medical instrument sterilizing and washing method according to claim 1, wherein the electrolytically-generated water is temperature of at least 30° C.

6. A medical instrument sterilizing and washing apparatus, comprising:

a circulation passage for sterilizing and washing water in which a halide is dissolved;

a medical instrument sterilizing and washing unit disposed at an arbitrary position in said circulation passage;

a pump unit for forcibly circulating the sterilizing and washing water;

an electrolytically-water-generating unit for causing the sterilizing and washing water to pass between an anode and a cathode in said circulation passage and subjecting the sterilizing and washing water to electrolysis whereby to generate electrolytically-generated water containing hypohalogenous acid;

pH detection means for detecting hydrogen ion concentration (pH) of the sterilizing and washing water;

pH maintenance means for maintaining the hydrogen ion concentration (pH) of said sterilizing and washing water detected by said pH detection means to 6–8;

hypohalogenous acid detection means disposed at a specific position in said circulation passage for detecting concentration of the hypohalogenous acid contained in the sterilizing and washing water;

timer means for measuring a specific period of time; and determination means and/or notification means for determining that sterilizing and washing processing has been completed when a specific hypohalogenous acid concentration is detected for a specific period of time at the specific position.

7. A medical instrument sterilizing and washing apparatus according to claim 6, wherein the halide is composed of a bromide component as a simple substance or a bromide compound and other halogenated compound.

8. A medical instrument sterilizing and washing apparatus according to claim 6, comprising temperature increasing means located at a specific position in said circulation passage for increasing the temperature of the sterilizing and washing water to at least 30°.

9. A medical instrument sterilizing and washing apparatus according to claim 6, comprising voltage measurement means for measuring an electric potential difference arisen when a constant current flows between the respective electrode plates of said electrolytically-water-generating unit and a dissolving amount control means for making the electric potential difference to a specific electric potential difference by controlling the amount of the halide to be added to and dissolved in the sterilizing and washing water.

10. A medical instrument sterilizing and washing apparatus according to claim 6, wherein said medical instrument sterilizing and washing unit additionally comprises ultrasonic wave generation unit for generating an ultrasonic wave and/or vibration means for applying vibration to a medical instrument.

11. A medical instrument sterilizing and washing apparatus according to claim 6, comprising at least one filter disposed at a specific position in said circulation passage for capturing an undissolved foreign material contained in the circulating sterilizing and washing water.

12. A medical instrument sterilizing and washing apparatus, comprising:

a circulation passage for sterilizing and washing water in which a halide is dissolved;

a medical instrument sterilizing and washing unit disposed at an arbitrary position in said circulation passage;

a pump unit for forcibly circulating the sterilizing and washing water;

an electrolytically-water-generating unit for causing the sterilizing and washing water to pass between an anode and a cathode in said circulation passage and subjecting the sterilizing and washing water to electrolysis whereby to generate electrically-generated water containing hypohalogenous acid;

pH detection means for detecting the hydrogen ion concentration (pH) in the sterilizing and washing water; and ratio adjustment means for changing the ratio of chloride and bromide to be dissolved in the sterilizing and washing water based on the hydrogen ion concentration (pH) detected by said pH detection means;

hypohalogenous acid detection means disposed at a specific position in said circulation passage for detecting concentration of the hypohalogenous acid contained in the sterilizing and washing water;

timer means for measuring a specific period of time; and determination means and/or notification means for determining that sterilizing and washing processing has been completed when a specific hypohalogenous acid concentration is detected for a specific period of time at the specific position.

* * * * *

UNITED STATES PATENT AND TRADEMARK OFFICE
CERTIFICATE OF CORRECTION

PATENT NO.    : 6,106,691
DATED         : August 22, 2000
INVENTOR(S)   : Nakamura et al.

It is certified that error appears in the above-identified patent and that said Letters Patent is hereby corrected as shown below:

<u>Title page,</u>
Inventors: change Hukuzuka" to read -- Fukuzuka --.

<u>Column 17,</u>
Line 3, insert -- spaced -- before "electrode".
Line 44, insert -- heated to a -- after "is".

Signed and Sealed this

Eighteenth Day of June, 2002

Attest:

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.   : 6,106,691
DATED        : August 22, 2000
INVENTOR(S)  : Nakamura et al.

Page 1 of 1

It is certified that error appears in the above-identified patent and that said Letters Patent is hereby corrected as shown below:

<u>Title page,</u>
Item [73], Assignee, change "T.R.P Co., Ltd." to read -- Omega Co., Ltd. --.

Signed and Sealed this

Tenth Day of September, 2002

*Attest:*

*Attesting Officer*

JAMES E. ROGAN
*Director of the United States Patent and Trademark Office*